Figure 1:
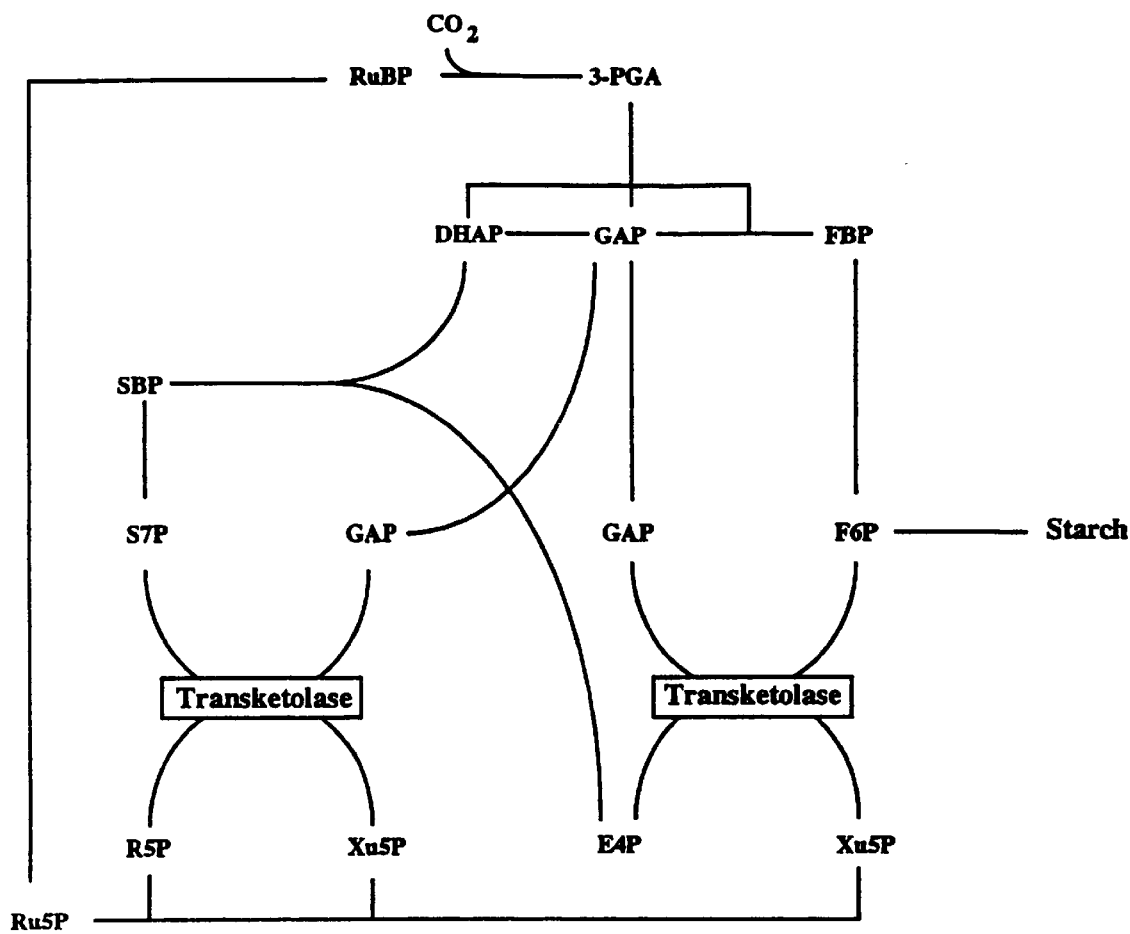
Figure 2:
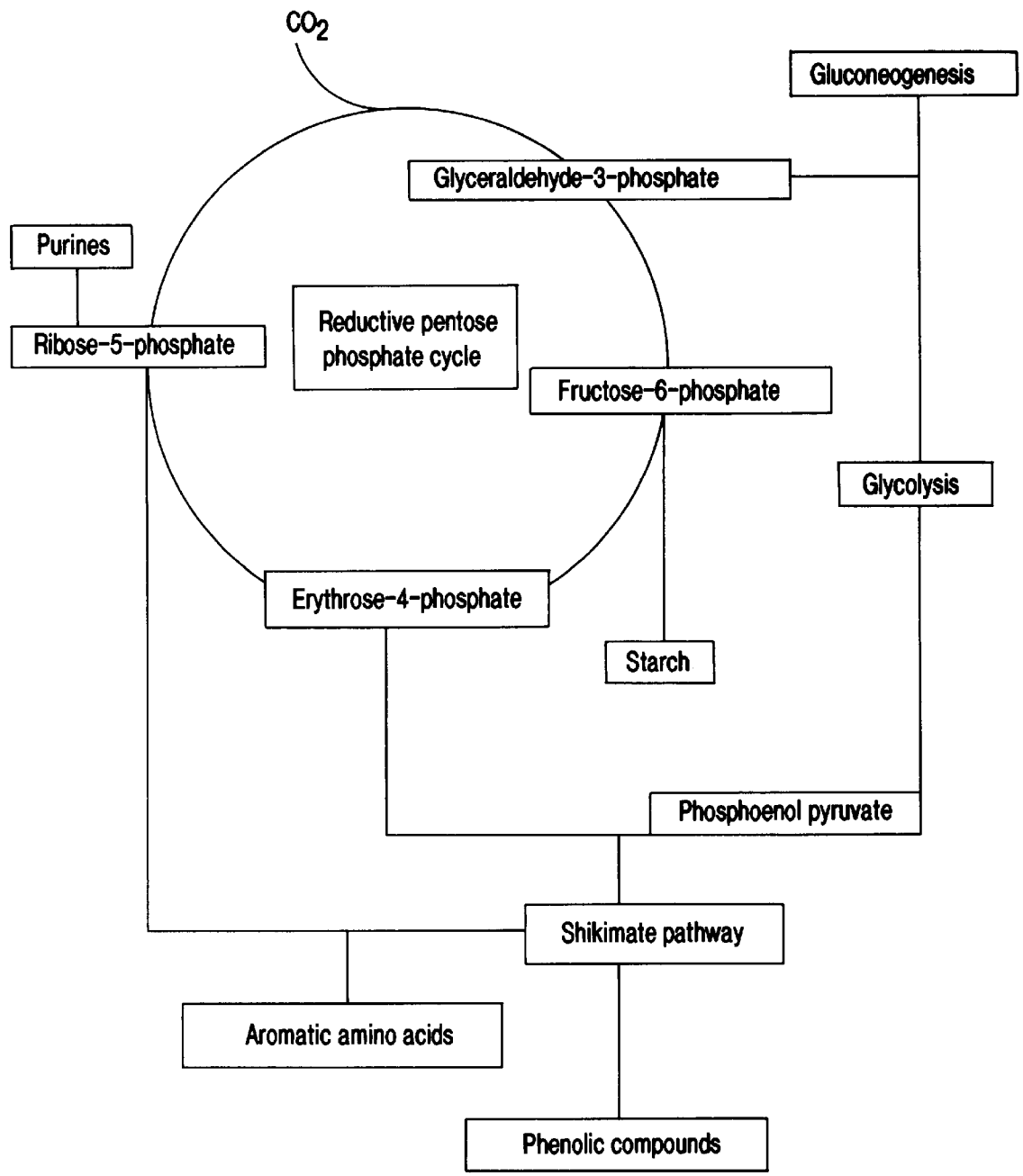

United States Patent [19]
Schmidt et al.

[11] Patent Number: 5,912,169
[45] Date of Patent: Jun. 15, 1999

[54] TRANSKETOLASE

[75] Inventors: Ralf-Michael Schmidt, Neustadt; Marc Stitt, Dossenheim; Uwe Sonnewald, Hoym, all of Germany

[73] Assignee: BASF Aktiengesellschaft, Ludwigshafen, Germany

[21] Appl. No.: 09/012,030

[22] Filed: Jan. 22, 1998

Related U.S. Application Data

[62] Division of application No. 08/590,454, Jan. 23, 1996.

[30] Foreign Application Priority Data

Jan. 23, 1995 [DE] Germany ................... 19501906

[51] Int. Cl.$^6$ ............ C12N 15/00; C12N 9/10; C07H 21/04
[52] U.S. Cl. ............ 435/320.1; 536/23.2; 435/193
[58] Field of Search ................ 435/193, 172.3, 435/172.2, 41, 252.1, 252.3; 935/22–24, 66, 76, 79

[56] References Cited

U.S. PATENT DOCUMENTS 5,168,056  12/1992  Frost ..................... 435/172.3

OTHER PUBLICATIONS

Sprenger, G.A. Nucleotide sequence of the *Escherichia coli* K–12 transketolase (tkt) gene. Biochemica et Biophysica Acta 1216:307–310, 1993.

*Primary Examiner*—Robert A. Wax
*Assistant Examiner*—Devesh Srivastava
*Attorney, Agent, or Firm*—Keil & Weinkauf

[57] ABSTRACT

A protein having transketolase activity, containing an amino acid sequence which is a part sequence of at least 100 amino acids from SEQ ID NO 2, and nucleic acids coding for this protein and its use are described.

3 Claims, 12 Drawing Sheets

```
   1 CTCCTCTTCA CTCTCTTTTC TCTTTGAGAC AAAACATCAA ACACCTTACT   50
  51 GGTAAAGCCA TGGCGTCTTC TTCTTCTCTC ACTCTCTCTC AAGCTATCCT  100
 101 CTCTCGTTCT GTCCCTCGCC ATGGCTCTGC CTCTTCTTCT CAACTTTCCC  150
 151 CTTCTTCTCT CACTTTTTCC GGCCTTAAAT CCAATCCCAA TATCACCACC  200
 201 TCCCGCCGCC GTACTCCTTC CTCCGCCGCC GCCGCCGCCG TCGTAAGGTC  250
 251 ACCGGCGATT CGTGCCTCAG CTGCAACCGA AACCATAGAG AAAACTGAGA  300
 301 CTGCGCTTGT TGACAAATCT GTAAACACGA TTCGATTTTT GGCTATTGAT  350
 351 GCTGTTGAAA GGCAAATTCG GGTCACCCGG TTTGCCATGG GTTGTGCTCC  400
 401 GATGGGTCAT ATATTGTACG ATGAGGTTAT GAGGTATAAC CCGAAAAACC  450
 451 CGTATTGGTT TAATCGGGAT CGGTTTGTTC TATCAGCTGG ACATGGTTGT  500
 501 ATGCTTCAGT ATGCTTTGCT TCATCTAGCT GGCTATGATG CTGTCAGGGA  550
 551 AGAGGACTTG AAGAGCTTCC GTCAGTGGGG AAGCAAAACC CCTGGACACC  600
 601 CTGAAAACTT TGAGACACCT GGTGTTGAAG TCACCACCGG GCCTCTGGA   650
 651 CAAGGTATTG CCAACGCCGT TGGCTTGGCT CTTGTGGAGA AACACTTGGC  700
 701 TGCTCGTTTC AATAAGCCTG ACGCTGAGAT TGTAGACCAC TACACATATG  750
 751 TTATTCTCGG TGATGGTTGC CAGATGGAGG GTATTTCACA AGAAGCTTGT  800
 801 TCCCTTGCTG GACACTGGGG ACTTGGAAAG CTGATTGCTT TCTATGATGA  850
 851 CAACCACATC TCAATTGATG GTGACACAGA AATCGCTTTC ACTGAGGATG  900
 901 TTGGTGCCCG TTTTGAGGCT CTTGGGTGGC ACGTAATCTG GGTGAAGAAC  950
 951 GGTAACACTG GTTATGATGA GATTCGTGCT GCTATTAAGG AAGCAAAAAC 1000
1001 TGTCACAGAC AAACCCACTA TGATCAAGGT GACTACAACC ATTGGTTTTG 1050
1051 GCTCGCCCAA CAAGGCAAAC AGTTACAGTG TACATGGAAG TGCACTTGGA 1100
1101 GCTAAGGAAG TAGAGGCCAC CAGGAGTAAC TTGGGATGGC CTTATGAGCC 1150
1151 TTTCCATGTG CCTGAAGATG TCAAGAGCCA TTGGAGTCGT CATGTTCCCG 1200
1201 AGGGTGCTGC TCTTGAAGCT GGGTGGAATA CCAAGTTTGC TGAATATGAG 1250
1251 AAGAAGTACC CAGAGGAAGC TGCAGAACTC AAATCCATTA CTACTGGTGA 1300
1301 ACTACCTGCT GGCTGGGAGA AAGCTCTTCC TACCTACACA CCTGAAAGTC 1350
1351 CAGCGGATGC CACCAGAAAC CTGTCCCAAC AAAACCTGAA TGCTCTTGCC 1400
1401 AAGGTTCTTC CTGGTTTCCT TGGTGGTAGT GCTGATCTTG CCTCATCAAA 1450
1451 CATGACCCTC ATGAAAATGT TTGGTGACTT CCAAAAGAAC ACCCCAGAGG 1500
1501 AGCGTAATCT AAGGTTTGGT GTTCGTGAAC ATGGTATGGG AGCCATATGT 1550
1551 AATGGTAATG CTCTACACAG CCCTGGCTTG ATTCCCTACT GTGCTACTTT 1600
1601 CTTTGTGTTC ACCGACTACA TGAGAGGAGC TATGAGAATT TCAGCCTTGT 1650
1651 CTGAGGCTGG AGTTATTTAT GTTATGACCC ACGATTCAAT TGGTCTAGGA 1700
1701 GAAGATGGGC CTACCCATCA ACCCATTGAG CACTTGGCAA GTTTCCGTGC 1750
1751 AATGCCCAAC ATTCTGATGT TCCGTCCAGC AGATGGCAAG GAGACAGCGG 1800
1801 GAGCTTACAA GGTGGCTGTC CTCAAGAGGA AGACACCATC AATCCTTGCC 1850
1851 CTCTCTCGGC AAAAGTTGCC ACAACTTGCT GGAAGTTCTA TTGAAGGAGC 1900
1901 AGCAAAGGGT GGCTACATTT TATCAGACAA TTCTTCTGGC AACAAACCTG 1950
1951 ATGTCATTTT GATTGGTACT GGCTCAGAGT TAGAAATTGC TGTCAAGGCT 2000
2001 GCTGATGAAC TCAGGAAAGA AGGAAAAGCA GTGAGAGTTG TTTCCTTTGT 2050
2051 TTGTTGGGAG CTTTTTGAAG AACAATCAGC CGACTACAAG GAAAGTGTCC 2100
2101 TTCCATCATC TGTTACAGCT AGAGTTAGCA TTGAGGCCGG ATCCACATTT 2150
2151 GGGTGGAGA AATATGTCGG ATCAAAGGGG AAGGCCATCG GAATTGACAG 2200
2201 ATGGGGTGCC AGTGCCCCTG CTGGAAAAAT ATACAAGGAG TACGGAATTA 2250
2251 CAGCAGAGGC TGTTGTAGCT GCAGCTAAAC AAGTTTCTTA GGCTTTATTA 2300
2301 CTTACCCTTG GTTGCTGGTG TCTACCAAAT TTGTTTTCAT TTTGAAACTG 2350
2351 AGGTTGGAGA TAACGGTGGA AACCAATACC AAACGGACTC GGCAGTTCAC 2400
2401 TGTTGCCTGG TATTTTCAAT AAAAACTATT TCTTCATCTG TCCTTTGTTT 2450
2451 TCTTCAGTTT TAGTAGCGGA GCGGCCAAAA TGAATCCAAG ATGAGGATAG 2500
2501 AAATAGGATT ATGGATGCTC CTGACCATGT ACACTTAAAA CATATCTGTG 2550
2551 AGTTTTGTAA TTTTATTTGG TCGAGTGATA CCAAGATCTC ATTTTCAATT 2600
2601 GGAAAAAAAA AAAAAAAAA AAAAAAAA                           2629
```

FIG. 3

Amino acid comparison of the plasmid transketolase from tobacco with transketolase isoenzymes from Saccaromyces cervesiae

```
TK-23    1                                               MASSSSL TLSQAILSRS    17

TK-23   18   VPRHGSASSS QLSPSSLTFS GLKSNPNITT SRRRTPSSAA AAAVVRSPAI RASAATETIE    77

TK-23   78   KTETALVDKS -VNTIRFLAI DAVERQIRVT RFAMGCAPMG HILYDEVMRY NPKNPYWFNR   136
TKL1     1   M.QFTDI..L A.S...I..V .T.SKANSGH PG.PLGMAPA AHVLWSQ..M .T.D.I...    60
TKL2     1   MAQFSDI..L A.S.L.L.SV .Q..SAQSGH PG.PLGLAPV AHVIFKQL.C ..N.EH.I...   60

TK-23  137   DRFVLSAGHG CMLQYALLHL AGYDAVREED LKSFRQWGSK TPGHPENFET PGVEVTIGPL   196
TKL1    61   ......N.A VA.L.SM... T...L-SI.. ..Q..L.R   ......-..L ..........   118
TKL2    61   ......N.S .A.L.SM... L...Y-SI.. .RQ...VN.R ......-HS A...I.S...   118

TK-23  197   GQGIANAVGL ALVEKHLAAR FNKPDAEIVD HYTYVILGDG CQMEGISQEA CSLAGHWGLG   256
TKL1   119   .S....M .MAQAN..T Y...GFTLS. N....F.... .LQ....S.. S......LK..   178
TKL2   119   .S....M .IAQANF..T Y.EDGFP.S. S..FA.V... .LQ..V.S.T S......LQ..   178

TK-23  257   KLIAFYDDNH ISIDGDTEIA FTEDVGARFE ALGWHVIWVK NGNTGYDEIR AAIKEAKTVT   316
TKL1   179   N..I....K T...A.S.S .D...AK.Y. .Y.E.LY.E ...EDLAG.A K..AQ..LSK   238
TKL2   179   N..T...S.S .....K.SYS .D...LK.Y. .Y.E.ME.D K.DDDMES.S S.LEK..LSK   238

TK-23  317   DKPTMIKVTT TIGFGSPNKA NSYSVHGSAL GAKEVEATRS NLGW-PYEPF HVPEDVKSHW   375
TKL1   239   ...L.M... ...Y..LHAG -.H....AP. K.DD.KQLKS KF.FN.DKS. V..QE.YDHY   297
TKL2   239   .....I.... ........ LQQG TA-G....... K.DD.KQLKK RW.FD.NKS. V..QE.YDYY   297
```

FIG. 4A

```
TK-23  376  SRHVPEGAAL EAG-WNTKFA EYEKKYPEEA AELKSITTGE LPAGWEKALP TYTPESPADA  434
TKL1   298  QKTILKPGVE ANNK.NKL.S ..Q..F..LG A..ARRLS.Q ...N..SK.. ...AKDS.V.  357
TKL2   298  KKT.V.PGQK LNEE.DR-.E ..KT.F..KG K..QRRLN.E ..E...KH.. KF..DDD.L.  356

TK-23  435  TRNLSQQNLN ALAKVLPGFL GGSADLASSN MTLMKMFGDF QKNTPEERN- LRFGVREHGM  493
TKL1   358  ..KL.ETV.E DVYNQ..ELI .......TP.. L.RWKEAL.. .PPSSGSG.Y SGRYI.YGIR  417
TKL2   357  ..KT...V.T NMVQV..ELI .......TP.. L.RWEGAV.. .PPITQLG.Y AGRYI.YGVR  416

TK-23  494  ---GAICNG NALHSPGLIP YCATFFVFTD YMRGAMRISA LSEAGVIYVM THDSIGLGED  549
TKL1   418  EHAM...M.. ISAFGANYK. .GG..LN.VS .AA..V.L.. ..GHP..W.A ......V...  477
TKL2   417  EHG-...M.. ISAFGANYK. .GG..LN.VS .AA..V.LA. ..GNP..W.A ..........  475

TK-23  550  GPTHQPIEHL ASFRAMPNIL MFRPADGKET AGAYKVAVLK RKTPSILALS RQKLPQLAGS  609
TKL1   478  .........T. .H..SL...Q VW.....N.V SA...NSLES KH.....I.. ...N....E.  537
TKL2   476  .........T. .HL..I..HV -W.....N.T SA..YS.IKS GR....VV.. ...N....EH.  534

TK-23  610  SIEGAAKGGY ILSDNSSGNK PDVILIGTGS ELEIAVKAAD ELR-KEGKAV RVVSFVCWEL  668
TKL1   538  ...S.S.... V.Q.VA---N ...I..VA... .VSLS.E..K T.AA.NI..- .....LPDFFT  593
TKL2   535  .F.K.L.... VIH.VE---N ...I..VS... .VS.SID..K K.YDTKKIKA ....LPDFYT  591

TK-23  669  FEEQSADYKE SVLPSSVTAR VSIEAGSTFG WEKYVGSKGK AIGIDRWGAS APAGKIYKEY  727
TKL1   595  .DK.PLE.RL ....DN.PIM -.V.VLA.TC .G..AHQSFG IDRFGAS.KA PEVF.FFGFT  652
TKL2   592  .DR..EE.RF ....DG.PIM -.F.VLA.SS .G..AHQSFG LDEFGRS.KG PEIY.LFDFT  650

TK-23  728  GITAEAVVAA AKQVS                                                    743
TKL1   653  PEGVAERAQK TIAFYKGDKL ISPLKKAF                                      680
TKL2   651  ADGVASRAEK TINYYKGKQL LSPMGRAF                                      678
```

FIG. 4B

TISSUE SPECIFIC EXPRESSION OF THE PLASTID TRANSKETOLASE IN TOBACCO PLANTS

LEGEND:

1: SINK LEAF
2: SOURCE LEAF
3: FLOWER BUD
4: INTERNODES
5: NODES
6: CORTEX
7: ROOT
8: OPEN FLOWER l-MCS: left polylinker sequence SacI------SacII------NotI------XbaI----SpeI----BamHI--SmaI----PstI-----EcoRI------NotI
5'- GAGCTCCACCGGTGGGGCCGCTCTAGAACTAGTGGATCCCCCGGGCTGCAGGAATTCGGGGCCGC-3' r-MCS: right polylinker sequence

SalI
NotI----EcoRI--EcoRV--HindIII------HincII------XhoI------------KpnI
5'- GCGGCCGCGAATTCGATATCAAGCTTATCGATACCGTCGACCTCGAGGGGGGCCCGGTACC -3'

Construction of plant expression cassettes for the
antisense inhibition of plastid transketolase ANTISENSE INHIBITION OF THE PLASTID TRANSKETOLASE IN TRANSGENIC TOBACCO PLANTS: RNA ANALYSIS OF THE TRANSFORMANTS IN TISSUE CULTURE LEGEND: NUMBERS, DESIGNATION OF THE SINGLE INDEPENDENT TRANSFORMANTS; CON, NON-TRANSFORMED CONTROL; A AND B, ANTISENSE-CONSTRUCT TK-28; C AND D, ANTISENSE-CONSTRUCT TK-26

TRANSKETOLASE

This Application is a Divisional of Ser. No. 08/590,454, filed Jan. 23, 1996.

The present invention relates to proteins having transketolase activity, their use in test systems, and nucleic acids which code for these proteins.

Plants are able to synthesize organic compounds from atmospheric carbon dioxide using light energy with formation of oxygen. This process is called photosynthesis.

It is to be assumed that the efficient formation, utilization and distribution of the photosynthesis products severely affect the growth of a plant.

As plants are dependent on a functioning photosynthesis and comparable reactions do not occur in animal organisms, the photosynthesis apparatus presents itself as an ideal target for the use of herbicides.

The complex reactions which lead to carbon diioxide fixation are divided into light and dark reactions. The light reaction is used for making available energy in the form of ATP and reduction equivalents in the form of NADPH. In the dark reaction (reductive pentose phosphate cycle or Calvin cycle), these compounds are used for the synthesis of organic carbon compounds.

Some of the known herbicides (eg. dichlorophenylmethylurea or paraquat) act by inhibition of the light reaction. The dark reaction is not utilized as a point of attack for herbicides.

The enzyme reactions of the reductive pentose phosphate cycle are divided into three sections:

a) carboxylation b) reduction c) regeneration.

In carboxylation, carbon dioxide reacts with the acceptor molecule ribulose bisphosphate (RuBP), whereby two molecules of 3-phosphoglycerate (3-PGA) are formed. After phosphorylation, 3-PGA is then reduced to glyceraldehyde-3-phosphate (GAP). In the regeneration phase, the acceptor molecule RuBP is resynthesized from the GAP formed. Of six molecules of GAP formed, one molecule can be employed for other metabolic pathways.

A multiplicity of the enzymes involved in the reductive pentose phosphate cycle are potential points of attack for herbicides. Plastid transketolase, however, assumes a special position. Like transaldolase, transketolase (E.C. 2.2.1.1.) catalyzes two reactions:

(1) 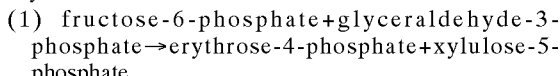

(2) 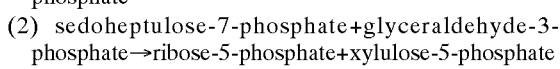

The substrates and products involved in the reactions represent points of linkage between the reductive pentose phosphate cycle and other metabolic pathways. Exported triose phosphates are used in the cytoplasm as substrates for glycolysis and gluconeogenesis. Fructose-6-phosphate is used as a precursor molecule for the preparation of starch in the plastids. Erythrose-4-phosphate is an intermediary between primary and secondary metabolism. Linked with phosphoenol pyruvate, erythrose-4-phosphate opens in the Shikimate pathway, which leads to the synthesis of aromatic amino acids and phenolic substances.

Ribose-5-phosphate is used as a substrate in different metabolic pathways.

In plant tissues, two transketolase isoforms were described which differ in their subcellular compartmentalization (Murphy and Walker, 1982, Planta 155, 316–320).

The plastid transketolase is responsible in green tissues for more than 75% of the total activity. The active enzyme is present as a homotetramer (holoenzyme) having a relative molecular weight of 150 kDa. As cofactors, transketolase needs vitamin $B_1$ (thiamine pyrophosphate) and magnesium. In the absence of thiamine pyrophosphate or in the presence of mercaptoethanol, the tetramer dissociates into two dimers (apoenzymes) having a relative molecular weight of 74 kDa each. Holo- and apoenzyme are catalytically active, the holoenzyme having a substantially higher activity than the apoenzyme.

Genes which code for transketolase were previously isolated from *Saccharomyces cerevisiae* (Flechter et al., Biochemistry 31, (1993), 1892–1896; Sundström et al., J. Biol. Chem. 268, (1993), 24346–24352; Schaff-Gerstenschläger et al., Eur. J. Biochem. 217, (1993), 487–492), from Hansenula polymorpha (Janowicz et al., Nucl. Acids Res. 13, (1985), 3043–3062), human erythrocytes (Abedinia et al., Biochem. Biophys. Res. Commun. 183, (1992), 1159–1166; McCool et al., J. Biol. Chem. 268, (1993), 1397–1404), *Rhodobacter sphaeroides* (Chen et al., J. Biol. Chem. 266, (1992), 20447–20452) and *Escherichia coli* (Sprenger, Biochem. Biophys. Acta 1216, (1992), 307–310; Tida et al., J. Bacteriol. 175, (1993), 5375–5383) and described. Genes of plant transketolases were unknown until now.

It is an object of the present invention to make available a plant transketolase in pure form by cloning the corresponding gene.

We have now found that this object is achieved by a protein having transketolase activity, containing the amino acid sequence shown in SEQ ID NO 2.

The amino acid sequence shown in SEQ ID NO 2 is based on the translation of the cDNA sequence shown in SEQ ID NO 1.

The protein shown in SEQ ID NO 2 is a precursor protein consisting of 743 amino acids. The mature protein is obtainable from the precursor form by removing the chloroplastid transit peptide, which according to a computer analysis consists of the 77 N-terminal amino acids.

Both the precursor protein and proteins derived therefrom by substitution, deletion or insertion of amino acids which still have a transketolase activity belong to the proteins according to the invention.

Substitution is understood as meaning the replacement of one or more amino acids by one or more other amino acids. Preferably, conservative replacements are carried out in which the replaced amino acid has similar properties to the original amino acid, for example replacement of Glu by Asp, Val by Ile, and Ser by Thr.

Deletion is the replacement of an amino acid by a direct bond; preferred positions for deletions are the termini of the polypeptide and the linkages between the individual protein domains.

Insertions are insertions of amino acids into the polypeptide chain, in which a direct bond is formally replaced by one or more amino acids.

Particularly preferred proteins are those which are formed from SEQ ID NO 2 by N-terminal shortening by from 20 to 100 amino acids.

The invention further relates to nucleic acids which code for the abovementioned proteins. Suitable nucleic acid sequences are obtainable by back-translation of the polypeptide sequence according to the genetic code. Preferably, those codons are used for this purpose which are frequently used according to the organism-specific codon usage. The codon usage can easily be determined with the aid of computer analyses of other known genes of the organism concerned.

If the plant transketolase is to be expressed, for example, in a bacterium, it is often advantageous to use the codon usage of the bacterium in the back-translation.

The invention further relates to vectors which contain the nucleic acids coding for the transketolase according to the invention together with functional regulation signals.

These are to be understood as meaning, for example, signals for transcription and translation such as promoters and ribosome binding sites or sequences necessary for replication or integration.

The proteins according to the invention are particularly suitable for the identification of herbicidal active compounds, in particular for the discovery of transketolase-specific inhibitors.

To this end, the proteins can be employed, for example, in an enzyme test in which the activity of the transketolase is determined in the presence and absence of the active compound to be tested. From comparison of the two activity determinations, a qualitative and quantitative conclusion can be made about the inhibitory behavior of the active compound to be tested.

Using the test system according to the invention, a multiplicity of chemical compounds can be investigated for herbicidal properties rapidly and simply.

The invention further relates to herbicides which are identifiable using a test system described above.

The invention additionally consists in a process for preparing herbicides which inhibit a plant transketolase, which comprises investigating known chemical compounds in a test process described above and formulating as herbicides those having inhibitory action using customary carriers and auxiliaries.

The fact that the transketolase-inhibiting properties of a substance alone are not adequate for suitability as a herbicide, but still further tests have to be carried out is familiar to any person skilled in the art.

The process makes possible, however, the reproducible selection from a large number of substances of specifically those having high potency in order subsequently to carry out using these substances further in-depth tests familiar to the person skilled in the art.

The invention is further illustrated by the following examples.

EXAMPLES

A. Recombinant DNA methods on which Exemplary Embodiments B are based

1. General cloning methods

Cloning methods such as eg. restriction cleavages, agarose gel electrophoresis, purification of DNA fragments, transfer of nucleic acids to nitrocellulose and nylon membranes, linkage of DNA fragments, transformation of *E. coli* cells, culture of bacteria, replication of phages and sequence analysis of recombinant DNA were carried out as described in Sambrook et al. (1989) (Cold Spring Harbor Laboratory Press: ISBN 0-87969-309-6). Transformation and culture of *Pichia pastoris* was carried out according to the details of the marketing company (Invitrogen Corporation). The transformation of *Agrobacterium tumefaciens* was carried out according to the method of Höfgen and Willmitzer (Nucl. Acid Res. (1988) 16, 9877). The culture of agrobacteria was carried out in YEB medium (Vervliet et al. J. Gen. Virol. (1975) 26, 33).

2. Generation of cDNA libraries

For preparation of leaf-specific cDNA libraries, total RNA from tobacco leaves was isolated according to a method described by Logemann et al. (Anal. Biochem. (1987) 163,21). The poly(A)-RNA was then purified on oligo(dT)-cellulose type 7 (Pharmacia, Freiburg) according to the details of the manufacturer. After photometric concentration determination, 5 μg of the RNA thus obtained were employed for the cDNA synthesis. All chemicals and enzymes necessary for the preparation of the cDNA were supplied by the company Stratagene (La Jolla Calif. 92037, USA). The methods used were carried out according to the details of the manufacturer. The synthesis of the first and second strand of the cDNA was carried out using the ZAP-cDNA synthesis kit. The double-stranded cDNAs obtained were then provided with EcoRI-NotI adaptors and cloned in an EcoRI-cleaved Lambda ZAPII vector. After in vitro packing (Gigapack II packing extract) of the recombinant lambda DNA, XL-1 *E. coli* cells (Stratagene) were transformed. By counting the plaques formed the titer of the cDNA libraries was determined.

3. Inspection of a cDNA library by means of heterologous DNA probes $2 \times 10^5$ recombinant lambda phages (Lambda ZapII) of a leaf-specific cDNA library from tobacco (variety Samsun NN) were plated out on agar plates. The phage DNA was transferred by means of standard methods (Sambrook et al. (1989); Cold Spring Harbor Laboratory Press: ISBN 0-87969-309-6) to nylon membranes (Hybond N, Amersham Buchler) and fixed to the filters by incubation for 2 hours at 80° C. The hybridization probes used were DNA fragments which were radiolabeled using a multiprime DNA labeling system (Amersham Buchler) in the presence of $\alpha$-$^{32}$P-dCTP (specific activity 3000 Ci/mmol) according to details of the manufacturer. Hybridization of the membrane was carried out after prehybridization at 42° C. in PEG buffer (Amasino (1986) Anal. Biochem. 152, 304–307) for 12–16 hours. The filters were then washed at 42° C. for 3×20 minutes in 2×SSC, 0.1% SDS. Positively hybridizing phages were visualized by autoradiography and purified by standard techniques.

4. Sequence analysis of recombinant DNA

The sequencing of recombinant DNA molecules was carried out using an automatic laser fluorescence DNA sequencer (A.L.F.) from Pharmacia using fluorescence-labeled oligonucleotides according to the method of Sanger (Sanger et al. (1977) Proc. Natl. Acad. Sci. USA 74, 5463–5467).

5. Bacterial strains and yeast strains

*E. coli* (XL-1 Blue) bacteria were supplied by Stratagene. The *Agrobacterium tumefaciens* strain employed for the plant transformation (C58Cl containing the plasmid pGV 3850 kan) was described by Debleare et al. (1985, Nucl. Acid Res. 13, 4777). Pichia pastoris strain GS115 was supplied by Invitrogen Corporation (San Diego, Calif. 92121, USA).

6. Tobacco transformation

For the transformation of tobacco plants (*Nicotiana tabacum* L. cv. Samsun NN), 10 ml of an overnight culture of *Agrobacterium tumefaciens* grown under selection were centrifuged off, the supernatant was discarded, and the bacteria were resuspended in the same volume of antibiotic-free medium. Leaf disks of sterile plants (diameter about 1 cm) were bathed in this bacteria solution in a sterile Petri dish. The leaf disks in Petri dishes were then put into MS medium (Murashige and Skoog, Physiol. Plant. (1962) 15,473) containing 2% sucrose and 0.8% Bacto agar. After incubation in the dark at 25° C. for 2 days, they were transferred to MS medium containing 100 mg/l of kanamycin, 500 mg/l of claforan, 1 mg/ml of benzylaminopurine (BAP), 0.2 mg/l of naphthylacetic acid (NAA), 1.6% glucose and 0.8% Bacto agar and culturing was continued (16 hours light/8 hours darkness). Growing shoots were transferred to hormone-free MS medium using 2% sucrose, 250 mg/l claforan and 0.8% Bacto agar.

7. Analysis of total RNA from plant tissues

Total RNA from plant tissues was isolated as described in Logemann et al. (Anal. Biochem. (1987) 163,21). For the analysis, 20–40 μg of RNA were in each case separated in a formaldehyde-containing 1.5% strength agarose gel. After electrophoretic separation of the RNA molecules, the RNA was transferred to a nylon membrane by means of capillary transfer. The detection of specific transcripts was carried out as described in Amasino (Anal. Biochem. (1986) 152, 304). The cDNA fragments employed as a probe were radiolabeled using a random primed DNA labeling kit (Boehringer, Mannheim).

8. PCR amplification of nucleic acids

Figure 9:
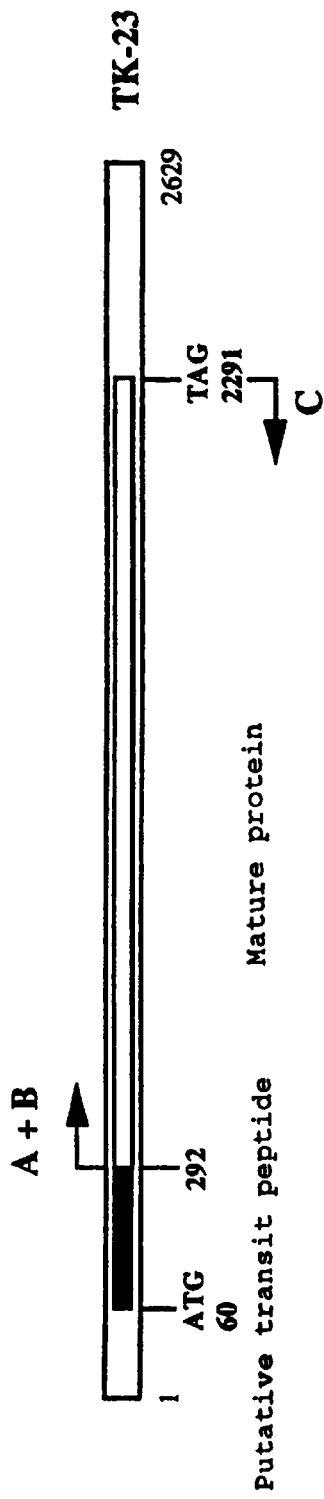

The PCR amplification of the transketolase for the expression of the enzyme in E. coli and Pichia was carried out in a DNA thermal cycler from Perkin Elmer. The oligonucleotides used are shown in FIG. 9. The reaction mixtures contained 1 ng of template, 0.5 μM of the corresponding oligonucleotides, 0.25 mM of nucleotides (Pharmacia), amplification buffer (16 mM $(NH_4)_2SO_4$, 67 mM tris HCl (pH 8.8 at 25° C.), 0.01% Tween 20, 7.5 MM $MgCl_2$) and 2.5 units of the Tth DNA polymerase (Biomaster, Crottorfer Str. 25, 51109 Cologne). The amplification conditions were adjusted as follows:

Addition temperature: 60° C.
Denaturation temperature: 94° C.
Elongation temperature: 72° C.
Number of cycles: 30

9. Overexpression of proteins in E. coli

For the overexpression of the transketolase in E. coli, 2 ml of an overnight culture which was cultured at 28° C. were transferred to 20 ml of growth medium (LB medium completed using 10 μg/ml of tetracycline 200 μg/ml of ampicillin, 1 mM vitamin B1 and 1 mM $MgSO_4$). Growth took place at 28° C. with shaking. After 3 hours, the expression of the transketolase was induced by addition of 2 mM IPTG. The detection of the protein produced was carried out by separating the proteins in an SDS PAAG (Laemmli (1970) Nature 227, 680–685) with subsequent Coomassie staining of the proteins.

B. Exemplary embodiments

1. Cloning of the plastid transketolase

A clone which codes for transketolase was selected from a leaf-specific cDNA library from tobacco (variety Samsun NN). The DNA sequence is shown in SEQ ID NO 1.

The cDNA clone 21 of length 2629 base pairs contains an open reading frame of 2229 bases and codes for a protein having 743 amino acids. Analysis of the polypeptide using the sequence program PC/gene (submenu TRANSPEP) showed that a chloroplastid transit peptide of presumably 77 amino acids is present at the N-terminus of the protein.

2. Comparison of the plastid transketolase from tobacco with known transketolase protein sequences Comparisons of homology of the derived amino acid sequence of the clone TK-23 (MacMolly sequence analysis program from Macintosh) with published transketolase sequences showed that the highest homologies to transketolases from Saccharomyces cervesiae exist in the area of the supposedly mature polypeptide (amino acids 78 to 743) (FIG. 4). The sequence of the mature protein (determined by computer prediction) is identical to 47.7% and 44.1% respectively with the transketolase 1 and 2 sequences of Saccharomyces cervesiae. Fewer sequence homologies were found for the other transketolases. No sequence homology was determined for the region of the transit peptide.

3. Expression analysis of the plastid transketolase

Figure 5:
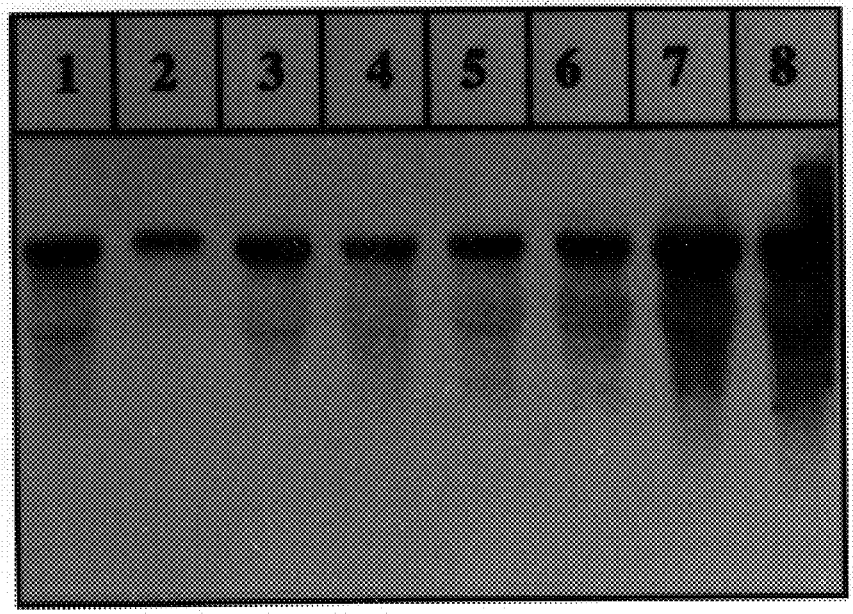

Expression analyses of some enzymes (RUBISCO, FBPase) involved in the Calvin cycle have shown that the accumulation of the corresponding transcripts is tied to green tissue and light. For monitoring the tissue-specific expression of the transketolase in tobacco plants, total RNA was isolated from sink leaves, source leaves, flower buds, stalks (internodes, nodes and cortex), roots and open flowers of growing tobacco plants. After separating in agarose gels and binding the RNA to nylon membranes, the presence of transketolase-specific transcripts was detected by hybridization with the radioactive TK-23 cDNA. As shown in FIG. 5, transketolase-specific transcripts are detectable in all organs tested. This result illustrates that in contrast to other enzymes of the Calvin cycle, transketolase in addition to its function in the Calvin cycle fulfills other objects in plant metabolism.

4. Antisense inhibition of transketolase in transgenic tobacco plants

Figure 6:
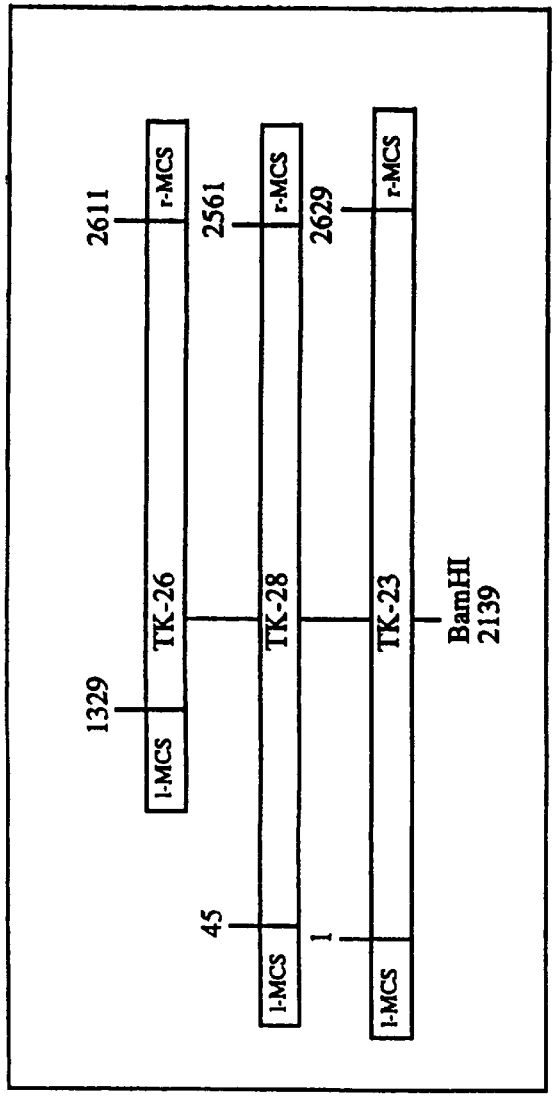
Figure 7A:
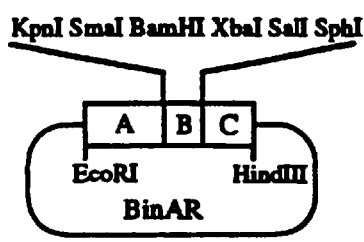

In order to produce transgenic tobacco plants having decreased transketolase activity, the cDNA clones TK-26 and TK-28 were provided in antisense direction with a promoter effecting constitutive expression and a plant termination signal. The plasmids BinAR-anti-TK-26 and BinAR-anti-TK-28 consisting of the three fragments A, the respective cDNA (see FIG. 6, TK-26 and TK-28) and C were produced by insertion of the corresponding cDNA sequences into the expression vector pBinAR (FIG. 7A).

Figure 7B:
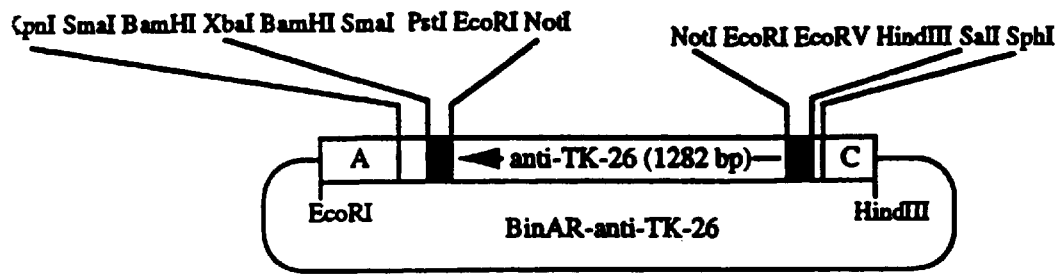
Figure 7C:
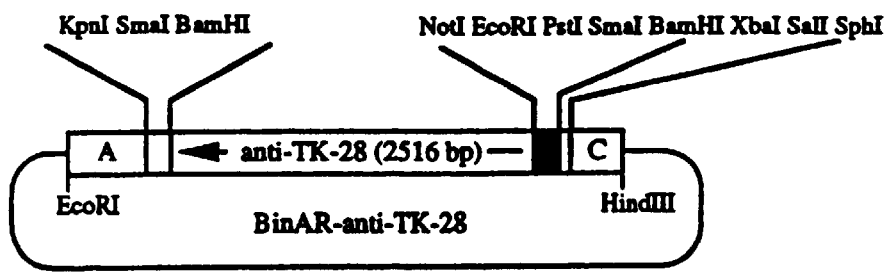

The fragment A comprises the 35S CaMV promoter. It contains a fragment which comprises the nucleotides 6909 to 7437 of the cauliflower mosaic virus (CaMV) (Franck et al. (1980) Cell 21, 285). It was isolated as an EcoRI-KpnI fragment from the plasmid pDH51 (Pietrzak et al. (1986) Nucleic. Acid Res. 14, 5857). The TK-26 cDNA was cloned in the pBinAR vector from the pBluescript SK (FIG. 6) as an XbaI-SalI fragment and the TK-28 cDNA as a BamHI fragment in the antisense direction (FIG. 7B and C). The fragment C contains the polyadenylation signal of the gene 3 of the T-DNA of the Ti plasmid pTiACH5 (Gielen et al. (1984); EMBO J. 3, 835), nucleotides 11749–11939, which has been isolated as a PvuII-HindIII fragment from the plasmid pAGV 40 (Herrera-Estrella et al. (1983); Nature 303,209) and after addition of SphI linkers had been cloned in the PvuII cleavage site between the SpHI-HindIII cleavage site of the vector.

Figure 8:
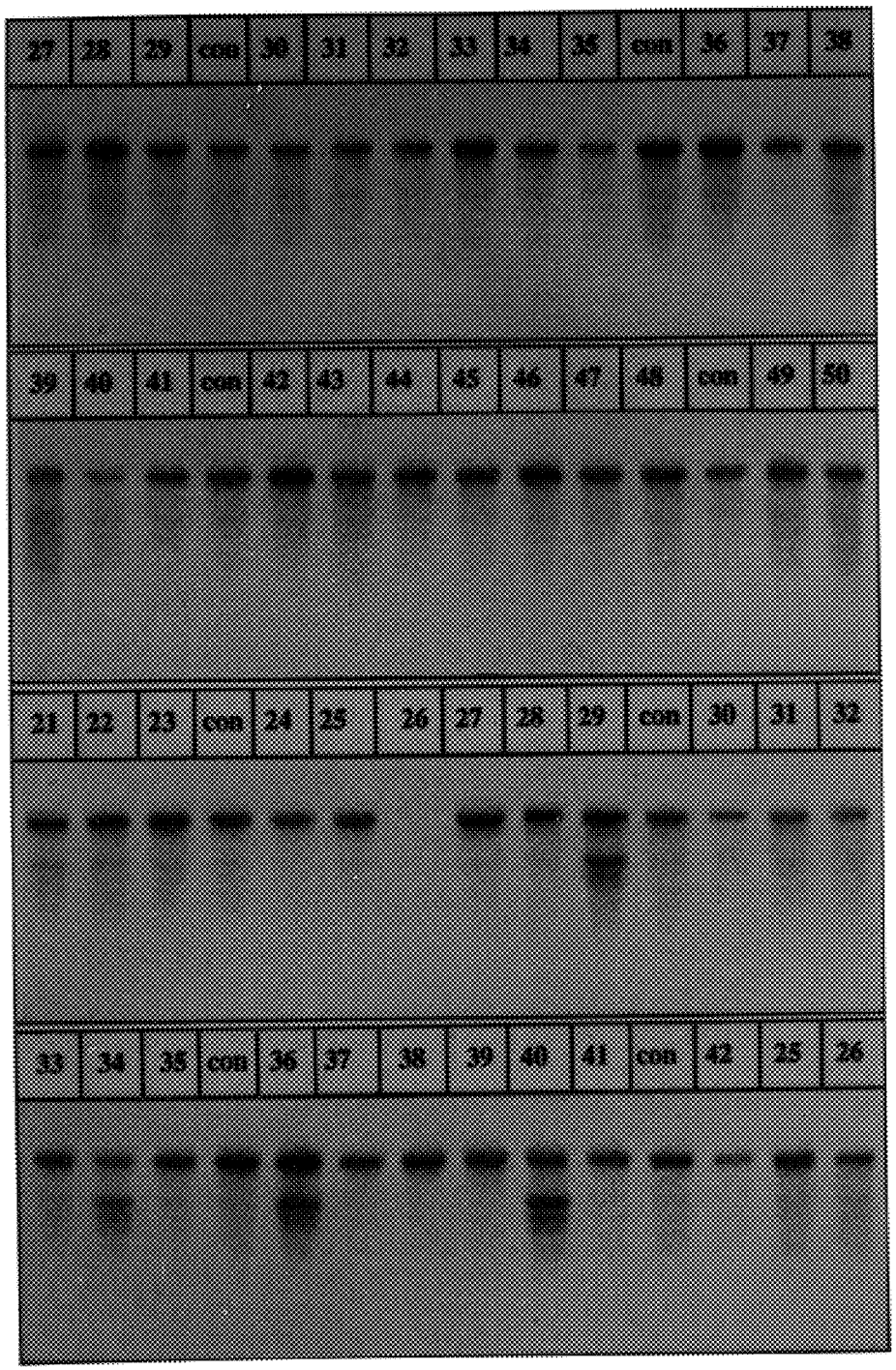

The plasmids obtained were transformed in tobacco using the Agrobacterium system. Transformed tobacco plants were raised on antibiotic-containing medium and the successful inhibition of transketolase was ascertained by determination of the amount of transcript by means of Northern experiments. For each transformation (TK-26 and TK-28) 100 independent transformants were investigated. FIG. 8 shows the result of a Northern experiment. In most regenerated plants no reduction in the transketolase mRNA could be detected. Some of the plants, however, showed a greater decrease in transketolase-specific transcripts (eg. anti-TK-26 No. 26; FIG. 8). The reduction of the amount of transcript led to a suppression of plant growth. Transfer of the plants into a greenhouse led to dying off of the inhibited plants.

5. Preparation of the plasmid TK23-AC-pQE-9

For establishment of a molecular test system the plant transketolase was overexpressed in microbial systems.

Figure 10:
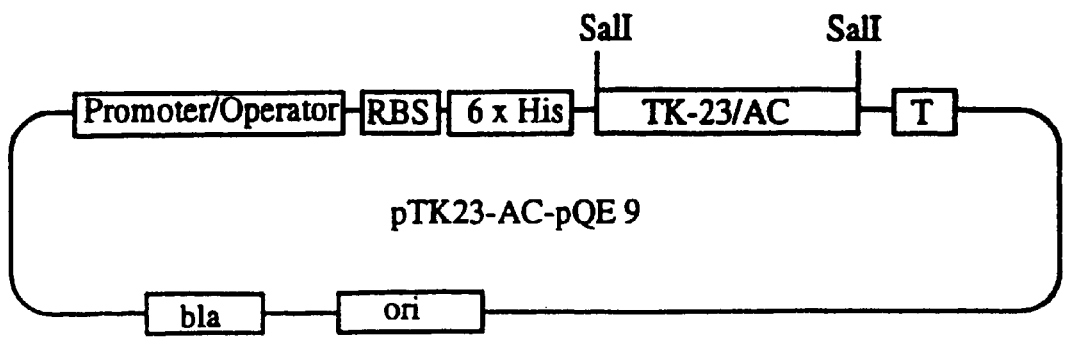

For expression of the transketolase in E. coli, the TK-23 sequence, which codes for the mature polypeptide, was amplified using the primers A and C (see FIG. 9) and cloned in the vector pGEM-T (recombinant DNA methods, section 8). The TK23-AC PCR amplification product was then cloned as an SalI fragment into the SalI cleavage site of the vector PQE-9 (DIAGEN GmbH, QLAGEN Inc.) (FIG. 10).

6. Preparation of the plasmid TK23-AC-pPIC-9 and TK23-BC-pHIL-D2

As eukaryotic enzymes can often only be expressed inadequately in bacterial systems, two further plasmid constructions were carried out which make possible expression in *Pichia pastoris* (strain GS115; Invitrogen Corporation San Diego, Calif. 92121, USA).

Figure 11:
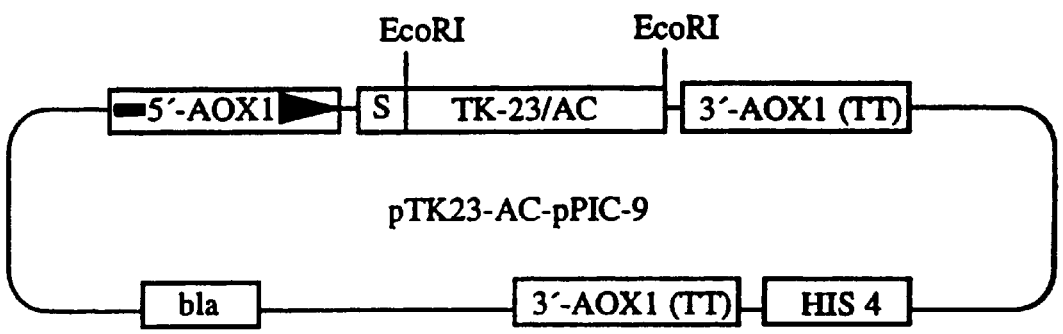
Figure 12:
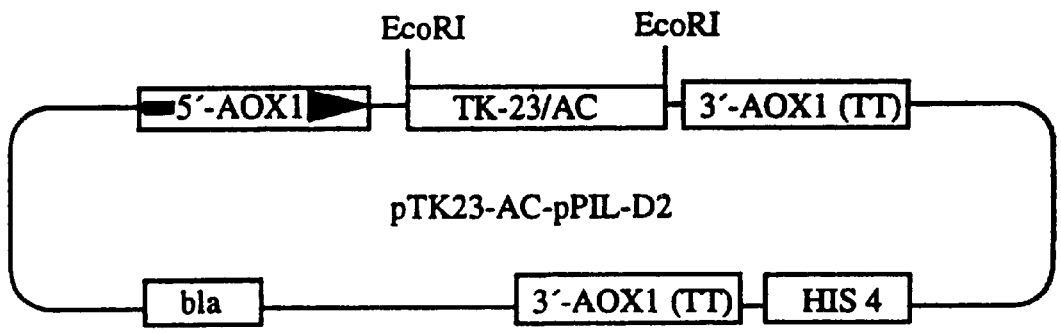

For secretion of the transketolase protein the plasmid TK23-AC-pPIC-9 was constructed. For fusion of the transketolase protein with a yeast signal peptide a part of the TK-23 sequence which codes for the mature polypeptide was amplified using the primers A and C (see FIG. 9) and cloned in the vector pGEM-T (recombinant DNA methods, section 8). The TK23-AC PCR amplification product was then cloned as an EcoRI fragment in the EcoRI cleavage site of the vector pPIC-9 of the Pichia expression kit (Invitrogen) (FIG. 11). In order to guarantee intracellular accumulation of the transketolase enzyme the plasmid TK23-BC-pHIL-D2 was prepared. For better purification of the enzyme a 5'-PCR primer (see FIG. 9) which contains a start codon for the translation and codes for six histidine radicals was used for amplification of the transketolase. After PCR amplification of the TK-23 sequence indicated in FIG. 9, the TK-23-BC product was cloned in the vector pGEM-T. The TK23-BC PCR amplification product was then cloned as an EcoRI fragment in the EcoRI cleavage site of the vector pHIL-D2 of the Pichia expression kit (Invitrogen) (FIG. 12).

7. Expression of the plant transketolase in *E. coli*

Figure 13:
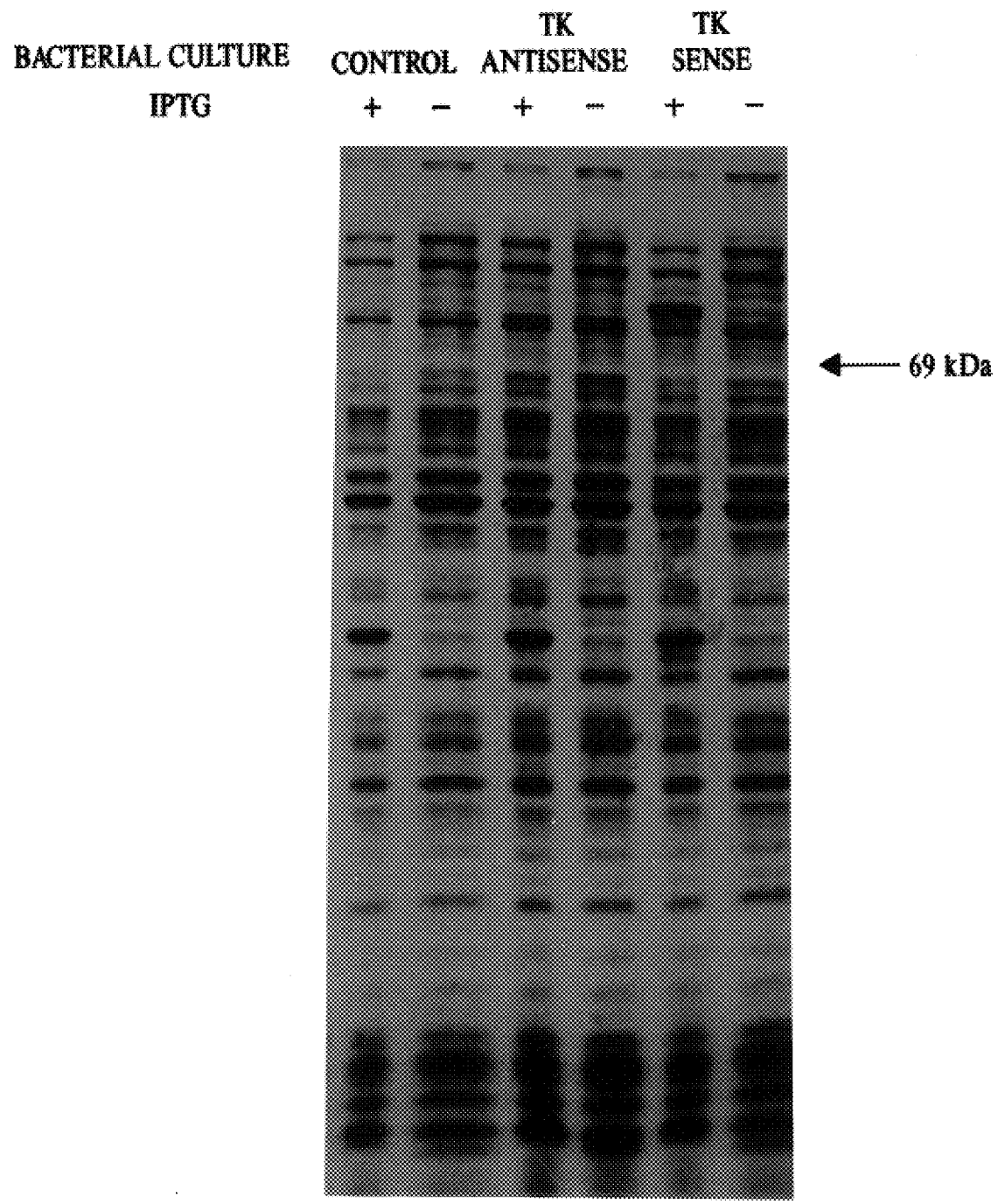

For overexpression of the transketolase in *E. coli* 2 ml of LB medium were inoculated with XL-1 *E. coli* cells which contained the plasmid TK23-AC-pQU-9. The cultures were grown overnight at 28° C. in the presence of antibiotics and with shaking. The overnight cultures were then transferred to 20 ml of growth medium (LB medium completed with: 10 $\mu$g/ml of tetracycline, 200 $\mu$g/ml of ampicillin, 1 mM vitamin $B_1$ and 1 mM $MgSO_4$). Growth took place at 28° C. with shaking. After 3 hours the expression of the transketolase was induced by addition of 2 mM IPTG. The detection of the protein produced was carried out by separating the proteins in an SDS PAAG (Laemmli (1970) Nature 227, 680–685) with subsequent Coomassie staining of the proteins. The controls used were cultures which were either not induced with IPTG or cultures which contained the transketolase in the antisense orientation. The result of an induction experiment is shown in FIG. 13. A protein of the appropriate size accumulated in bacterial cultures which were induced with IPTG and contained the plasmid TK23-AC-pQE-9. The accumulation begins an hour after induction. In the controls (without IPTG or transketolase in the antisense orientation) no comparable protein is identifiable.

FIGURES

1. Reductive pentose phosphate cycle

2. Linkage of the pentose phosphate cycle to other metabolic pathways

3. Nucleotide sequence of the plastid transketolase from tobacco

4. Amino acid comparison of the plastid transketolase with transketolase 1 and 2 from yeast 5. Detection of the transketolase mRNA in different tobacco tissues 6. Schematic representation of the transketolase cDNA clones 7. Schematic representation of the plasmids BinAR-TK-26-anti and BinAR-TK-28-anu 8. Northern analysis of transgenic tobacco plants 9. Strategy and oligonucleotides for the PCR amplification of plastid transketolase 10. Schematic representation of the plasmid TK23-AC-pQE-9

11. Schematic representation of the plasmid TK23-AC-pPIC-9

12. Schematic representation of the plasmid TK23-BC-pHIL-D2

13. Overexpression of plant transketolase in *E. coli*

---

We claim:

1. An isolated nucleic acid coding for a protein having transketolase activity, comprising an amino acid sequence of at least 100 amino acids from SEQ ID NO 2.

2. A nucleic acid as claimed in claim 1, which consists of the sequence shown in SEQ ID NO 1.

3. A vector containing a nucleic acid as claimed in claim 1 or together with functional regulation signals.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 2629 base pairs
      (B) TYPE: nucleic acid
      (C) STRANDEDNESS: single
      (D) TOPOLOGY: linear (ii) MOLECULE TYPE: cDNA (iii) HYPOTHETICAL: No (vi) ORIGINAL SOURCE:
      (A) ORGANISM: Nicotiana (ix) FEATURE:
      (A) NAME/KEY: CDA
      (B) LOCATION: 60..2289

(xi) SEQUENCE DESCRIPTION: SEQ ID NO: 1:

```
CTCCTCTTCA CTCTCTTTTC TCTTTGAGAC AAAACATCAA ACACCTTACT GGTAAAGCC             59

ATG GCG TCT TCT TCT TCT CTC ACT CTC TCT CAA GCT ATC CTC TCT CGT            107
Met Ala Ser Ser Ser Ser Leu Thr Leu Ser Gln Ala Ile Leu Ser Arg
 1               5                  10                  15

TCT GTC CCT CGC CAT GGC TCT GCC TCT TCT TCT CAA CTT TCC CCT TCT            155
Ser Val Pro Arg His Gly Ser Ala Ser Ser Ser Gln Leu Ser Pro Ser
                 20                  25                  30

TCT CTC ACT TTT TCC GGC CTT AAA TCC AAT CCC AAT ATC ACC ACC TCC            203
Ser Leu Thr Phe Ser Gly Leu Lys Ser Asn Pro Asn Ile Thr Thr Ser
             35                  40                  45

CGC CGC CGT ACT CCT TCC TCC GCC GCC GCC GCC GTC GTA AGG TCA                251
Arg Arg Arg Thr Pro Ser Ser Ala Ala Ala Ala Val Val Arg Ser
     50                  55                  60

CCG GCG ATT CGT GCC TCA GCT GCA ACC GAA ACC ATA GAG AAA ACT GAG            299
Pro Ala Ile Arg Ala Ser Ala Ala Thr Glu Thr Ile Glu Lys Thr Glu
 65                  70                  75                  80

ACT GCG CTT GTT GAC AAA TCT GTA AAC ACG ATT CGA TTT TTG GCT ATT            347
Thr Ala Leu Val Asp Lys Ser Val Asn Thr Ile Arg Phe Leu Ala Ile
                 85                  90                  95

GAT GCT GTT GAA AGG CAA ATT CGG GTC ACC CGG TTT GCC ATG GGT TGT            395
Asp Ala Val Glu Arg Gln Ile Arg Val Thr Arg Phe Ala Met Gly Cys
                100                 105                 110

GCT CCG ATG GGT CAT ATA TTG TAC GAT GAG GTT ATG AGG TAT AAC CCG            443
Ala Pro Met Gly His Ile Leu Tyr Asp Glu Val Met Arg Tyr Asn Pro
            115                 120                 125

AAA AAC CCG TAT TGG TTT AAT CGG GAT CGG TTT GTT CTA TCA GCT GGA            491
Lys Asn Pro Tyr Trp Phe Asn Arg Asp Arg Phe Val Leu Ser Ala Gly
        130                 135                 140

CAT GGT TGT ATG CTT CAG TAT GCT TTG CTT CAT CTA GCT GGC TAT GAT            539
His Gly Cys Met Leu Gln Tyr Ala Leu Leu His Leu Ala Gly Tyr Asp
145                 150                 155                 160

GCT GTC AGG GAA GAG GAC TTG AAG AGC TTC CGT CAG TGG GGA ACC AAA            587
Ala Val Arg Glu Glu Asp Leu Lys Ser Phe Arg Gln Trp Gly Thr Lys
                165                 170                 175

ACC CCT GGA CAC CCT GAA AAC TTT GAG ACA CCT GGT GTT GAA GTC ACC            635
Thr Pro Gly His Pro Glu Asn Phe Glu Thr Pro Gly Val Glu Val Thr
                180                 185                 190

ACC GGG CCT CTG GGA CAA GGT ATT GCC AAC GCC GTT GGC TTG GCT CTT            683
Thr Gly Pro Leu Gly Gln Gly Ile Ala Asn Ala Val Gly Leu Ala Leu
            195                 200                 205

GTG GAG AAA CAC TTG GCT GCT CGT TTC AAT AAG CCT GAC GCT GAG ATT            731
Val Glu Lys His Leu Ala Ala Arg Phe Asn Lys Pro Asp Ala Glu Ile
        210                 215                 220

GTA GAC CAC TAC ACA TAT GTT ATT CTC GGT GAT GGT TGC CAG ATG GAG            779
Val Asp His Tyr Thr Tyr Val Ile Leu Gly Asp Gly Cys Gln Met Glu
225                 230                 235                 240

GGT ATT TCA CAA GAA GCT TGT TCC CTT GCT GGA CAC TGG GGA CTT GGA            827
Gly Ile Ser Gln Glu Ala Cys Ser Leu Ala Gly His Trp Gly Leu Gly
                245                 250                 255

AAG CTG ATT GCT TTC TAT GAT GAC AAC CAC ATC TCA ATT GAT GGT GAC            875
Lys Leu Ile Ala Phe Tyr Asp Asp Asn His Ile Ser Ile Asp Gly Asp
                260                 265                 270

ACA GAA ATC GCT TTC ACT GAG GAT GTT GGT GCC CGT TTT GAG GCT CTT            923
Thr Glu Ile Ala Phe Thr Glu Asp Val Gly Ala Arg Phe Glu Ala Leu
            275                 280                 285

GGG TGG CAC GTA ATC TGG GTG AAG AAC GGT AAC ACT GGT TAT GAT GAG            971
Gly Trp His Val Ile Trp Val Lys Asn Gly Asn Thr Gly Tyr Asp Glu
        290                 295                 300

ATT CGT GCT GCT ATT AAG GAA GCA AAA ACT GTC ACA GAC AAA CCC ACT           1019
Ile Arg Ala Ala Ile Lys Glu Ala Lys Thr Val Thr Asp Lys Pro Thr
```

```
            305                 310                 315                 320
ATG ATC AAG GTG ACT ACA ACC ATT GGT TTT GGC TCG CCC AAC AAG GCA           1067
Met Ile Lys Val Thr Thr Thr Ile Gly Phe Gly Ser Pro Asn Lys Ala
                        325                 330                 335

AAC AGT TAC AGT GTA CAT GGA AGT GCA CTT GGA GCT AAG GAA GTA GAG           1115
Asn Ser Tyr Ser Val His Gly Ser Ala Leu Gly Ala Lys Glu Val Glu
                        340                 345                 350

GCC ACC AGG AGT AAC TTG GGA TGG CCT TAT GAG CCT TTC CAT GTG CCT           1163
Ala Thr Arg Ser Asn Leu Gly Trp Pro Tyr Glu Pro Phe His Val Pro
                    355                 360                 365

GAA GAT GTC AAG AGC CAT TGG AGT CGT CAT GTT CCC GAG GGT GCT GCT           1211
Glu Asp Val Lys Ser His Trp Ser Arg His Val Pro Glu Gly Ala Ala
                370                 375                 380

CTT GAA GCT GGG TGG AAT ACC AAG TTT GCT GAA TAT GAG AAG AAG TAC           1259
Leu Glu Ala Gly Trp Asn Thr Lys Phe Ala Glu Tyr Glu Lys Lys Tyr
385                 390                 395                 400

CCA GAG GAA GCT GCA GAA CTC AAA TCC ATT ACT ACT GGT GAA CTA CCT           1307
Pro Glu Glu Ala Ala Glu Leu Lys Ser Ile Thr Thr Gly Glu Leu Pro
                        405                 410                 415

GCT GGC TGG GAG AAA GCT CTT CCT ACC TAC ACA CCT GAA AGT CCA GCG           1355
Ala Gly Trp Glu Lys Ala Leu Pro Thr Tyr Thr Pro Glu Ser Pro Ala
                    420                 425                 430

GAT GCC ACC AGA AAC CTG TCC CAA CAA AAC CTG AAT GCT CTT GCC AAG           1403
Asp Ala Thr Arg Asn Leu Ser Gln Gln Asn Leu Asn Ala Leu Ala Lys
                435                 440                 445

GTT CTT CCT GGT TTC CTT GGT GGT AGT GCT GAT CTT GCC TCA TCA AAC           1451
Val Leu Pro Gly Phe Leu Gly Gly Ser Ala Asp Leu Ala Ser Ser Asn
            450                 455                 460

ATG ACC CTC ATG AAA ATG TTT GGT GAC TTC CAA AAG AAC ACC CCA GAG           1499
Met Thr Leu Met Lys Met Phe Gly Asp Phe Gln Lys Asn Thr Pro Glu
465                 470                 475                 480

GAG CGT AAT CTA AGG TTT GGT GTT CGT GAA CAT GGT ATG GGA GCC ATA           1547
Glu Arg Asn Leu Arg Phe Gly Val Arg Glu His Gly Met Gly Ala Ile
                    485                 490                 495

TGT AAT GGT AAT GCT CTA CAC AGC CCT GGC TTG ATT CCC TAC TGT GCT           1595
Cys Asn Gly Asn Ala Leu His Ser Pro Gly Leu Ile Pro Tyr Cys Ala
                500                 505                 510

ACT TTC TTT GTG TTC ACC GAC TAC ATG AGA GGA GCT ATG AGA ATT TCA           1643
Thr Phe Phe Val Phe Thr Asp Tyr Met Arg Gly Ala Met Arg Ile Ser
            515                 520                 525

GCC TTG TCT GAG GCT GGA GTT ATT TAT GTT ATG ACC CAC GAT TCA ATT           1691
Ala Leu Ser Glu Ala Gly Val Ile Tyr Val Met Thr His Asp Ser Ile
        530                 535                 540

GGT CTA GGA GAA GAT GGG CCT ACC CAT CAA CCC ATT GAG CAC TTG CCA           1739
Gly Leu Gly Glu Asp Gly Pro Thr His Gln Pro Ile Glu His Leu Pro
545                 550                 555                 560

AGT TTC CGT GCA ATG CCC AAC ATT CTG ATG TTC CGT CCA GCA GAT GGC           1787
Ser Phe Arg Ala Met Pro Asn Ile Leu Met Phe Arg Pro Ala Asp Gly
                        565                 570                 575

AAG GAG ACA GCG GGA GCT TAC AAG GTG GCT GTC CTC AAG AGG AAG ACA           1835
Lys Glu Thr Ala Gly Ala Tyr Lys Val Ala Val Leu Lys Arg Lys Thr
                    580                 585                 590

CCA TCA ATC CTT GCC CTC TCT CGG CAA AAG TTG CCA CAA CTT GCT GGA           1883
Pro Ser Ile Leu Ala Leu Ser Arg Gln Lys Leu Pro Gln Leu Ala Gly
                595                 600                 605

AGT TCT ATT GAA GGA GCA GCA AAG CGT GGC TAC ATT TTA TCA GAC AAT           1931
Ser Ser Ile Glu Gly Ala Ala Lys Arg Gly Tyr Ile Leu Ser Asp Asn
            610                 615                 620

TCT TCT GGC AAC AAA CCT GAT GTC ATT TTG ATT GGT ACT GGC TCA GAG           1979
Ser Ser Gly Asn Lys Pro Asp Val Ile Leu Ile Gly Thr Gly Ser Glu
```

-continued

```
          625                630                635                640

TTA GAA ATT GCT GTC AAG GCT GCT GAT GAA CTC AGG AAA GAA GGA AAA         2027
Leu Glu Ile Ala Val Lys Ala Ala Asp Glu Leu Arg Lys Glu Gly Lys
                    645                650                655

GCA GTG AGA GTT GTT TCC TTT GTT TGT TGG GAG CTT TTT GAA GAA CAA         2075
Ala Val Arg Val Val Ser Phe Val Cys Trp Glu Leu Phe Glu Glu Gln
                660                665                670

TCA GCC GAC TAC AAG GAA AGT GTC CTT CCA TCA TCT GTT ACA GCT AGA         2123
Ser Ala Asp Tyr Lys Glu Ser Val Leu Pro Ser Ser Val Thr Ala Arg
            675                680                685

GTT AGC ATT GAG GCC GGA TCC ACA TTT GGG TGG GAG AAA TAT GTC GGA         2171
Val Ser Ile Glu Ala Gly Ser Thr Phe Gly Trp Glu Lys Tyr Val Gly
        690                695                700

TCA AAG GGG AAG GCC ATC GGA ATT GAC AGA TGG GGT GCC AGT GCC CCT         2219
Ser Lys Gly Lys Ala Ile Gly Ile Asp Arg Trp Gly Ala Ser Ala Pro
705                710                715                720

GCT GGA AAA ATA TAC AAG GAG TAC GGA ATT ACA GCA GAG GCT GTT GTA         2267
Ala Gly Lys Ile Tyr Lys Glu Tyr Gly Ile Thr Ala Glu Ala Val Val
                725                730                735

GCT GCA GCT AAA CAA GTT TCT T AGGCTTTATT ACTTACCCTT GGTTGCTGGT         2319
Ala Ala Ala Lys Gln Val Ser
                740

GTCTACCAAA TTTGTTTTCA TTTTGAAACT GAGGTTGGAG ATAACGGTGG AAACCAATAC      2379

CAAACGGACT CGGCAGTTCA CTGTTGCCTG GTATTTTCAA TAAAAACTAT TTCTTCATCT      2439

GTCCTTTGTT TTCTTCAGTT TTAGTAGCGG AGCGGCCAAA ATGAATCCAA GATGAGGATA      2499

GAAATAGGAT TATGGATGCT CCTGACCATG TACACTAAA ACATATCTGT GAGTTTTGTA       2559

ATTTTATTTG GTCGAGTGAT ACCAAGATCT CATTTTCAAT TGGAAAAAAA AAAAAAAAAA      2619

AAAAAAAAA                                                              2629

(2) INFORMATION FOR SEQ ID NO: 2:

(i) SEQUENCE CHARACTERISTICS:
        (A) LENGTH: 743 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Ser Ser Ser Leu Thr Leu Ser Gln Ala Ile Leu Ser Arg
 1               5                  10                  15

Ser Val Pro Arg His Gly Ser Ala Ser Ser Gln Leu Ser Pro Ser
                20                  25                  30

Ser Leu Thr Phe Ser Gly Leu Lys Ser Asn Pro Asn Ile Thr Thr Ser
            35                  40                  45

Arg Arg Arg Thr Pro Ser Ala Ala Ala Ala Val Val Arg Ser
        50                  55                  60

Pro Ala Ile Arg Ala Ser Ala Ala Thr Glu Thr Ile Glu Lys Thr Glu
65                  70                  75                  80

Thr Ala Leu Val Asp Lys Ser Val Asn Thr Ile Arg Phe Leu Ala Ile
                85                  90                  95

Asp Ala Val Glu Arg Gln Ile Arg Val Thr Arg Phe Ala Met Gly Cys
                100                 105                 110

Ala Pro Met Gly His Ile Leu Tyr Asp Glu Val Met Arg Tyr Asn Pro
            115                 120                 125

Lys Asn Pro Tyr Trp Phe Asn Arg Asp Arg Phe Val Leu Ser Ala Gly
        130                 135                 140
```

His Gly Cys Met Leu Gln Tyr Ala Leu Leu His Leu Ala Gly Tyr Asp
145                 150                 155                 160

Ala Val Arg Glu Glu Asp Leu Lys Ser Phe Arg Gln Trp Gly Thr Lys
            165                 170                 175

Thr Pro Gly His Pro Glu Asn Phe Glu Thr Pro Gly Val Glu Val Thr
                180                 185                 190

Thr Gly Pro Leu Gly Gln Gly Ile Ala Asn Ala Val Gly Leu Ala Leu
            195                 200                 205

Val Glu Lys His Leu Ala Ala Arg Phe Asn Lys Pro Asp Ala Glu Ile
210                 215                 220

Val Asp His Tyr Thr Tyr Val Ile Leu Gly Asp Gly Cys Gln Met Glu
225                 230                 235                 240

Gly Ile Ser Gln Glu Ala Cys Ser Leu Ala Gly His Trp Gly Leu Gly
                245                 250                 255

Lys Leu Ile Ala Phe Tyr Asp Asp Asn His Ile Ser Ile Asp Gly Asp
                260                 265                 270

Thr Glu Ile Ala Phe Thr Glu Asp Val Gly Ala Arg Phe Glu Ala Leu
            275                 280                 285

Gly Trp His Val Ile Trp Val Lys Asn Gly Asn Thr Gly Tyr Asp Glu
290                 295                 300

Ile Arg Ala Ala Ile Lys Glu Ala Lys Thr Val Thr Asp Lys Pro Thr
305                 310                 315                 320

Met Ile Lys Val Thr Thr Thr Ile Gly Phe Gly Ser Pro Asn Lys Ala
                325                 330                 335

Asn Ser Tyr Ser Val His Gly Ser Ala Leu Gly Ala Lys Glu Val Glu
                340                 345                 350

Ala Thr Arg Ser Asn Leu Gly Trp Pro Tyr Glu Pro Phe His Val Pro
            355                 360                 365

Glu Asp Val Lys Ser His Trp Ser Arg His Val Pro Glu Gly Ala Ala
            370                 375                 380

Leu Glu Ala Gly Trp Asn Thr Lys Phe Ala Glu Tyr Glu Lys Lys Tyr
385                 390                 395                 400

Pro Glu Glu Ala Ala Glu Leu Lys Ser Ile Thr Thr Gly Glu Leu Pro
                405                 410                 415

Ala Gly Trp Glu Lys Ala Leu Pro Thr Tyr Thr Pro Glu Ser Pro Ala
            420                 425                 430

Asp Ala Thr Arg Asn Leu Ser Gln Gln Asn Leu Asn Ala Leu Ala Lys
            435                 440                 445

Val Leu Pro Gly Phe Leu Gly Gly Ser Ala Asp Leu Ala Ser Ser Asn
450                 455                 460

Met Thr Leu Met Lys Met Phe Gly Asp Phe Gln Lys Asn Thr Pro Glu
465                 470                 475                 480

Glu Arg Asn Leu Arg Phe Gly Val Arg Glu His Gly Met Gly Ala Ile
                485                 490                 495

Cys Asn Gly Asn Ala Leu His Ser Pro Gly Leu Ile Pro Tyr Cys Ala
                500                 505                 510

Thr Phe Phe Val Phe Thr Asp Tyr Met Arg Gly Ala Met Arg Ile Ser
            515                 520                 525

Ala Leu Ser Glu Ala Gly Val Ile Tyr Val Met Thr His Asp Ser Ile
            530                 535                 540

Gly Leu Gly Glu Asp Gly Pro Thr His Gln Pro Ile Glu His Leu Pro
545                 550                 555                 560

Ser Phe Arg Ala Met Pro Asn Ile Leu Met Phe Arg Pro Ala Asp Gly

```
                            565                    570                      575
Lys Glu Thr Ala Gly Ala Tyr Lys Val Ala Val Leu Lys Arg Lys Thr
            580                     585                 590

Pro Ser Ile Leu Ala Leu Ser Arg Gln Lys Leu Pro Gln Leu Ala Gly
        595                     600                 605

Ser Ser Ile Glu Gly Ala Ala Lys Arg Gly Tyr Ile Leu Ser Asp Asn
        610                     615                 620

Ser Ser Gly Asn Lys Pro Asp Val Ile Leu Ile Gly Thr Gly Ser Glu
625                     630                     635                     640

Leu Glu Ile Ala Val Lys Ala Ala Asp Glu Leu Arg Lys Glu Gly Lys
                645                     650                     655

Ala Val Arg Val Val Ser Phe Val Cys Trp Glu Leu Phe Glu Glu Gln
                660                     665                     670

Ser Ala Asp Tyr Lys Glu Ser Val Leu Pro Ser Ser Val Thr Ala Arg
            675                     680                     685

Val Ser Ile Glu Ala Gly Ser Thr Phe Gly Trp Glu Lys Tyr Val Gly
        690                     695                     700

Ser Lys Gly Lys Ala Ile Gly Ile Asp Arg Trp Gly Ala Ser Ala Pro
705                     710                     715                     720

Ala Gly Lys Ile Tyr Lys Glu Tyr Gly Ile Thr Ala Glu Ala Val Val
                725                     730                     735

Ala Ala Ala Lys Gln Val Ser
                740
```